United States Patent [19]
Miller

[11] Patent Number: 5,915,966
[45] Date of Patent: Jun. 29, 1999

[54] TOOTH CROWN PREPARATION SYSTEM

[76] Inventor: William J. Miller, 22 Chelsea Ct., Sewell, N.J. 08080

[21] Appl. No.: 09/150,606

[22] Filed: Sep. 10, 1998

[51] Int. Cl.[6] .............................. A61C 17/06; A61C 1/16
[52] U.S. Cl. ............................. 433/125; 433/91; 433/116
[58] Field of Search .................................... 433/116, 125, 433/131, 91, 121, 166, 130

[56] References Cited

U.S. PATENT DOCUMENTS

| | | | |
|---|---|---|---|
| 1,834,726 | 12/1931 | Ozon | 433/116 |
| 2,655,725 | 10/1953 | Fehrman | 433/116 |
| 2,703,904 | 3/1955 | DeLong | 433/91 |
| 3,126,021 | 3/1964 | May | 433/116 |
| 3,786,566 | 1/1974 | Jelicic et al. | 433/116 |
| 3,822,432 | 7/1974 | Skinner | 433/125 |
| 4,219,619 | 8/1980 | Zarow | 433/118 |
| 4,281,989 | 8/1981 | Glover et al. | 433/130 |
| 4,424,036 | 1/1984 | Lokken | 433/116 |
| 5,040,977 | 8/1991 | Weissman | 433/125 |
| 5,145,367 | 9/1992 | Kasten | 433/91 |
| 5,318,445 | 6/1994 | Meier et al. | 433/121 |
| 5,342,196 | 8/1994 | Van Hale | 433/91 |
| 5,547,376 | 8/1996 | Harrel | 433/116 |

*Primary Examiner*—Paul J. Hirsch

[57] ABSTRACT

A tooth crown preparation system is provided including a handle and a tooth cover fixed to the handle and defining an interior space and an open bottom. A grinding assembly is rotatably mounted to the handle and situated within the tooth cover for rotating upon its actuation to grind a tooth situated within the interior space of the tooth cover. A plurality of tooth covers and grinding assemblies are included for affording a system which may accommodate various sized teeth. Also provided is a suction assembly for removing particles from within the grinding assembly.

14 Claims, 2 Drawing Sheets

TOOTH CROWN PREPARATION SYSTEM

BACKGROUND OF THE INVENTION

1. Field of the Invention

The present invention relates to dental tools and more particularly pertains to a new tooth crown preparation system for preparing a tooth stump for a crown.

2. Description of the Prior Art

The use of dental tools is known in the prior art. More specifically, dental tools heretofore devised and utilized are known to consist basically of familiar, expected and obvious structural configurations, notwithstanding the myriad of designs encompassed by the crowded prior art which have been developed for the fulfillment of countless objectives and requirements.

Known prior art dental tools include U. S. Pat. No. 3,979,829; U.S. Pat. No. 4,194,291; U.S. Pat. No. 4,701,128; U.S. Pat. No. 3,011,259; U.S. Pat. No. 2,176,339; and Foreign Patents WO 96/23450 & WO 89/09574.

In these respects, the tooth crown preparation system according to the present invention substantially departs from the conventional concepts and designs of the prior art, and in so doing provides an apparatus primarily developed for the purpose of preparing a tooth stump for a crown.

SUMMARY OF THE INVENTION

In view of the foregoing disadvantages inherent in the known types of dental tools now present in the prior art, the present invention provides a new tooth crown preparation system construction wherein the same can be utilized for preparing a tooth stump for a crown.

The general purpose of the present invention, which will be described subsequently in greater detail, is to provide a new tooth crown preparation system apparatus and method which has many of the advantages of the dental tools mentioned heretofore and many novel features that result in a new tooth crown preparation system which is not anticipated, rendered obvious, suggested, or even implied by any of the prior art dental tools, either alone or in any combination thereof.

To attain this, the present invention generally comprises a handle comprising a hollow outboard extent with a generally rectangular configuration. As shown the Figures, the outboard extent of the handle has a top face, a bottom face and a thin periphery formed therebetween. Such periphery is defined by a pair of elongated side faces, a short rear face and a tapering front face. The handle further includes a hollow inboard extent with a rectangular configuration. The inboard extent ideally has a length equal to that of the outboard extent and a width about ⅓ that of the outboard extent. Further, the inboard extent is pivotally coupled to the front face of the outboard extent. Next provided is a tooth cover including an elastomeric sleeve having a generally square horizontal cross-section along a height thereof. The sleeve has a top end removably mounted to a bottom face of the inboard extent of the handle adjacent to a front face thereof. As shown in FIG. 5, the sleeve defines an interior space and an open bottom. A pair of gum line protective flaps are integrally coupled to a front face and a rear face of the sleeve of the tooth cover and extended downwardly therefrom. FIG. 5 best shows a grinding assembly of the present invention which includes a grinding unit rotatably, slidably and removably mounted to the inboard extent of the handle. As shown in FIG. 5, the grinding unit has a hollow frustoconical configuration with a plurality of apertures formed therein. The grinding unit is situated within the tooth cover. In use, the grinding unit serves to rotate upon its actuation for the purpose of grinding a tooth. For affording control of the grinding unit, the grinding assembly further includes a plurality of push button momentary switches situated on the top face of the handle. Such push button switches may be depressed for selectively actuating the grinding unit. The push button momentary switches further operate to slide the grinding assembly within the tooth cover along an axis thereof. FIG. 5 shows a suction assembly including a conduit situated within the interior space of the handle. The conduit is equipped with a first open end extending from the bottom face of the inboard extent of the handle. The first open end of the conduit terminates within the tooth cover. Associated therewith is a second open end extending from the bottom face of the outboard extent of the handle adjacent to the rear face thereof for being releasably connected to a suction mechanism. As such, particles suctioned through the apertures of the grinding assembly may be removed. As an option, a valve may be situated along the conduit of the suction assembly for selectively allowing the vacuum to be present at the first open end. Similar to the grinding assembly, such valve would be control by way of a push button momentary switch situated on the handle.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new tooth crown preparation system apparatus and method which has many of the advantages of the dental tools mentioned heretofore and many novel features that result in a new tooth crown preparation system which is not anticipated, rendered obvious, suggested, or even implied by any of the prior art dental tools, either alone or in any combination thereof.

It is another object of the present invention to provide a new tooth crown preparation system which may be easily and efficiently manufactured and marketed.

It is a further object of the present invention to provide a new tooth crown preparation system which is of a durable and reliable construction.

An even further object of the present invention is to provide a new tooth crown preparation system which is susceptible of a low cost of manufacture with regard to both materials and labor, and which accordingly is then susceptible of low prices of sale to the consuming public, thereby making such tooth crown preparation system economically available to the buying public.

Still yet another object of the present invention is to provide a new tooth crown preparation system which provides in the apparatuses and methods of the prior art some of the advantages thereof, while simultaneously overcoming some of the disadvantages normally associated therewith.

Still another object of the present invention is to provide a new tooth crown preparation system for preparing a tooth stump for a crown.

Even still another object of the present invention is to provide a new tooth crown preparation system that includes a handle and a tooth cover fixed to the handle and defining an interior space and an open bottom. A grinding assembly is rotatably mounted to the handle and situated within the tooth cover for rotating upon its actuation to grind a tooth situated within the interior space of the tooth cover. A plurality of tooth covers and grinding assemblies are included for affording a system which may accommodate various sized teeth.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annnexed drawings wherein.

DESCRIPTION OF THE PREFERRED EMBODIMENT

Figure 1:
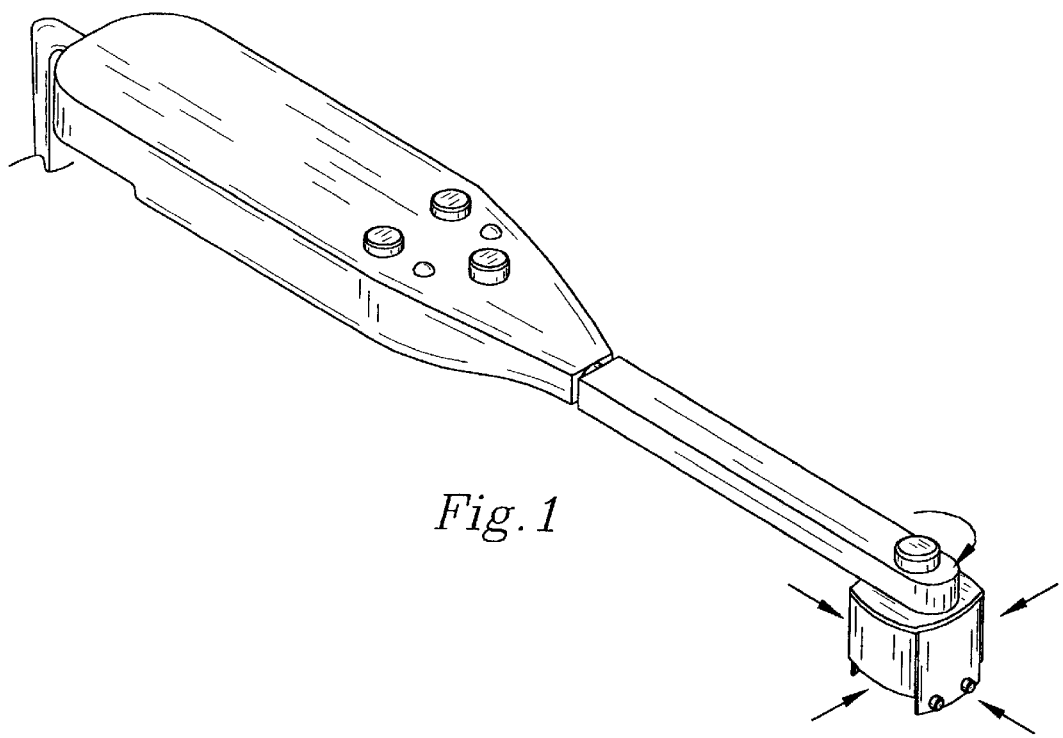
FIG. 1 is a perspective view of a new tooth crown preparation system according to the present invention.
Figure 2:
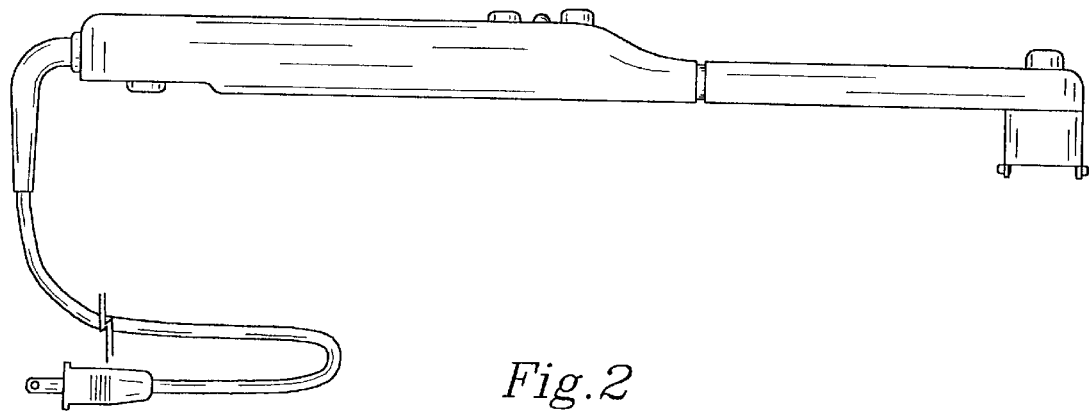
FIG. 2 is a side view of the present invention with an exploded view of the various tooth cover attachments of the present invention.
Figure 3:
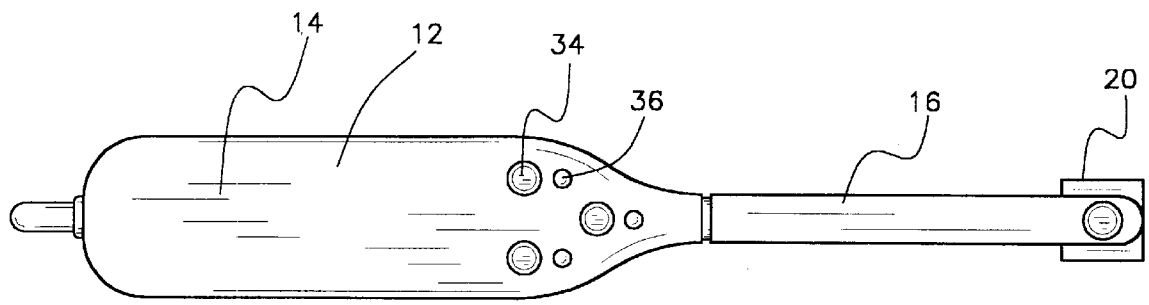
FIG. 3 is a top view of the present invention.
Figure 4:
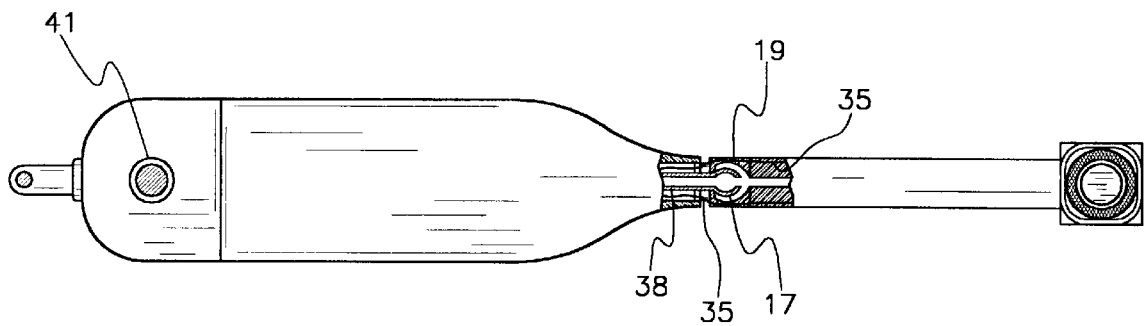
FIG. 4 is a bottom view of the present invention.

With reference now to the drawings, and in particular to FIGS. 1 through 5 thereof, a new tooth crown preparation system embodying the principles and concepts of the present invention and generally designated by the reference numeral 10 will be described.

The present invention, designated as numeral 10, includes a handle 12 comprising a hollow outboard extent 14 with a generally rectangular configuration. As shown the Figures, the outboard extent of the handle has a top face, a bottom face and a thin periphery formed therebetween. Such periphery is defined by a pair of elongated side faces, a short rear face and a tapering front face.

The handle further includes a hollow inboard extent 16 with a rectangular configuration. The inboard extent ideally has a length equal to that of the outboard extent and a width about ⅓ that of the outboard extent. Further, the inboard extent is pivotally and rotatably coupled to the front face of the outboard extent. Such pivotal coupling is preferably universal in nature. To accomplish this, the outboard extent may include a ball joint 17 which is attachable within a socket housing 19 formed in the inboard extent. Note FIG. 4. As an option, the socket housing may be threadedly coupled to the inboard extent. In the alternative, separate connections may be employed, one for motion, the other for the suction line. The connection and the release of the connection can be made through a turning motion such as in the case with a toothbrush manufactured by INTERPLAK by BAUSCH & LOMB. In yet another alternate embodiment, a connector with tits may be employed that has a button on the top ot the outboard extent to contract the tits to release the connection between both extents.

Figure 5:
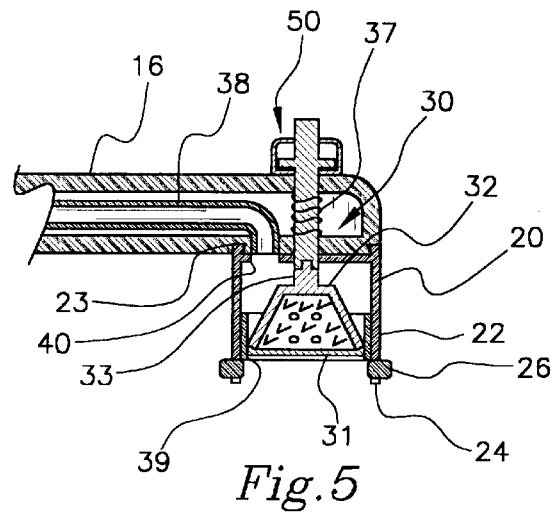
FIG. 5 is a cross-sectional view of the present invention taken along a vertical plane which bisects the tooth cover, grind assembly and handle.

Next provided is a tooth cover 20 including an elastomeric sleeve 22 having a generally square horizontal cross-section along a height thereof. The sleeve has a top end removably mounted to a bottom face of the inboard extent of the handle adjacent to a front face thereof. To accomplish such renovable coupling, the top face of the tooth cover may be equipped with any sort of coupling means including a pair of beveled protrusions 23 which are coupleable within beveled indentations formed in the housing. Note FIGS. 2 & 5. As an option, the beveled protrusions may be annular in form for allowing the rotation of the tooth cover. As shown in FIG. 5, the sleeve defines an interior space and an open bottom.

As an option, a height of the elastomeric sleeve may be made adjustable by various means. For example, height adjustability may be afforded by providing a telescoping sleeve which may be transferred between different discrete orientations using a spring biased mechanism or the like. Further, providing the sleeve with width adjustment may be considered if desired. It should be noted that height and width adjustment of the sleeve may also be afforded by simply providing multiple detachable tooth covers having different sizes.

A pair of gum line protective flaps 24 are integrally coupled to a front face and a rear face of the sleeve of the tooth cover and extended downwardly therefrom. Each protective flap has a pair of spaced set screws 26 for engaging a lower extent of a tooth when the same is positioned within the tooth cover. As an option, the present flaps are extensions of a pair of opposed guard plates 27 which line the front face and rear face of the sleeve of the tooth cover. Note FIG. 1. These guard plates serve to protect neighboring teeth during use.

FIG. 5 best shows a grinding assembly 30 of the present invention which includes a grinding unit 32 rotatably, slidably and removably mounted to the inboard extent of the handle. The grinding unit preferably has a protective bushling 31 mounted along a bottom peripheral edge thereof. As shown in FIG. 5, the grinding unit has a hollow frusto-conical configuration with a plurality of apertures formed therein. A post 33 is fixed to and extends upwardly front the grinding unit. The grinding assembly is situated within the tooth cover during operation. In use, the grinding unit serves to rotate for the purpose of grinding a tooth. To accomplish this, the grinding unit may be connected to a battery or AC-operated motor 50 situated within the inboard extent of the handle. As an option, the motor may be mounted within the outboard extent of the handle. To afford the removable coupling between the grinding assembly and the motor, a rotor of the motor and the post of the grinding assembly are equipped with a coupling 35 similar to that employed in the art of ratchets. In other words, square female and male couples are employed with some sort of detent/indent combination for securing such coupling. In the preferred embodiment, the grinding unit may also be adjusted along an axis about which it rotates. To accomplish this, the rotor of the motor is freely slidably within the stator of the motor. To control such sliding action, the rotor of the motor further has a solenoid coil 37 situated thereon. Such solenoid coil works to extend the grinding unit along its axis upon the actuation thereof. Yet another option may be entail making the grinding assembly adjustable by any means similar to that discussed hereinabove regarding the tooth covers.

For affording control of the grinding unit, the grinding assembly further includes a plurality of push button momentary switches 34 situated on the top face of the handle. Such push button switches may be depressed for selectively actuating the motor of the grinding unit. The push button momentary switches further operate to actuate the solenoid relay, thereby sliding the grinding assembly within the tooth cover along an axis thereof. Connection between the switches and the motor and solenoid is preferably accomplished by way of wires 35. Coils in the wires allow the relative rotation of the inboard and outboard extents. For protecting the joint and wires, an accordion-type sleeve may be formed about the same. As an option, indicator lights 36 may be employed to alert a user as to which stage the solenoid and motor are operating.

The manner in which the switches operate the solenoid and motor will now be set forth. A first switch is employed to actuate the solenoid, thereby lowering the grinding unit to rest on the tooth with a predetermined force. An associated light illuminates when the grinding unit is properly lowered. Further included is a second switch for actuating the motor. It should be noted that the motor may be actuated only after the solenoid is actuated. A critical feature of the motor is that it automatically deactuates when a torque is sensed indicating that grinding is complete. Such torque may be monitored by simply gauging the current within the motor. The second switch also has a light associated therewith to indicate that the motor is deactuated and grinding is complete. Finally, a third switch is included for deactuatinig the solenoid upon the depression thereof. The third switch also has all indicator light to convey that the solenoid has been deactuated. As an option, a spring may be mounted on the rotor for urging the grinding unit upwardly when the solenoid is deactuated.

FIG. 5 shows a suction assembly including a conduit 38 situated within the interior space of the handle. The conduit preferably remains in communication with the ball joint and socket housing. Note FIG. 4. The conduit is equipped with a first open end extending from the bottom face of the inboard extent of the handle. The first open end of the conduit preferably extends within at least one top hole 40 in the tooth cover. Associated therewith is a second open end extending from the bottom face of the outboard extent of the handle adjacent to the rear face thereof for being releasably connected to a suction mechanism. To better accomplish this, the second open end is preferably equipped with a female suction connector 41. As Such, particles may be suctioned through the apertures of the grinding assembly and removed. To afford a seal between a lower edge of the grinding unit and the tooth cover, a bushing 39 may be mounted about an inner periphery of the tooth cover. Such bushing is preferably equipped with a circular inner periphery for slidably abutting the grinding unit. As an option, a valve may be situated along the conduit of the suction assembly for governing the vacuum present at the first open end. Similar to the grinding assembly, such valve would be controlled by way of another push button momentary switch situated on the handle.

In use, the ability of the outboard extent to pivot with respect to the inboard extent provides the operator with convenience, visibility and versatility. Though both extents as an option could be one piece and less complicated, this would be more difficult for the operator to connect it to the tooth cover in difficult locations, unless an case of connection can be made without difficulty. The outboard extent has the ability to connect to the inboard extent with the controls of the outboard extent facing the operator when either the inboard extent is connected to the tooth cover for the top teeth or connected to the bottom teeth. Also, as an option, the inboard extent that connects to the tooth cover has the ability to swivel and pivot while the outboard extent remains stationary.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A tooth crown preparation system comprising, in combination:

a handle including a hollow outboard extent with a generally rectangular configuration having a top face, a bottom face and a thin periphery formed therebetween defined by a pair of elongated side faces, a short rear face and a tapering front face, the handle further including a hollow inboard extent with a rectangular configuration having a length equal to that of the outboard extend and a width about $\frac{1}{13}$ that of the outboard extent, the inboard extent being pivotally coupled to the front face of the outboard extent;

a tooth cover including an elastomeric sleeve having a generally square horizontal cross-section along a height thereof, the sleeve having a top end removably mounted to a bottom face of the inboard extent of the handle adjacent to a front face thereof and extending downwardly therefrom, thereby defining an interior space and an open bottom;

a pair of gum line protective flaps are integrally coupled to a front face and a rear face of the sleeve of the tooth cover and extended downwardly therefrom, each protective flap having a pair of spaced set screws for engaging a lower extent of a tooth when the same is positioned within the tooth cover;

a grinding assembly including a grinding unit with hollow frusto-conical configuration and a plurality of apertures formed therein, the grinding unit rotatably, slidably and removably mounted to the inboard extent of the handle and situated within the tooth cover for rotating upon its actuation for the purpose of grinding a tooth, wherein the grinding assembly further includes a plurality of push button momentary switches situated on the top face of the handle adjacent to the front face thereof for selectively actuating the grinding unit, wherein the push button momentary switches further operate to slide the grinding assembly within the tooth cover along an axis thereof; and a suction assembly including a conduit situated within the interior space of the handle with a first open end extending from the bottom face of the inboard extent of the handle and terminating within the tooth cover and a second open end extending from the bottom face of the outboard extent of the handle adjacent to the rear face thereof for being releasably connected to a suction mechanism such that particles may be suctioned through the apertures of the grinding assembly and removed.

2. A tooth crown preparation system comprising:

a handle;

a tooth cover mounted on the handle and defining an interior space and an open bottom;

a grinding assembly rotatably mounted to the handle and situated within the tooth cover for rotating upon its actuation to grind a tooth, wherein the grinding assembly has at least one aperture formed therein for allowing the passage of particles therethrough; and a suction assembly for removing particles from within the grinding assembly, the suction assembly including a conduit situated within an interior space of the handle with a first open end terminating within the tooth cover and a second open end extending from an outboard extent of the handle for being releasably connected to a suction mechanism such that particles within the grinding assembly are removed.

3. A tooth crown preparation system as set forth in claim 2 and further including a plurality of differently sized tooth covers and grinding assemblies which are removably coupled to the handle.

4. A tooth crown preparation system as set forth in claim 2 wherein at least one button is mounted on the handle for selectively actuating the grinding assembly.

5. A tooth crown preparation system as set forth in claim 2 wherein the grinding assembly is slidable along its axis and further included is at least one button mounted on the handle for selectively sliding the grinding assembly along its axis.

6. A tooth crown preparation system as set forth in claim 2 wherein the outboard extent of the handle is pivotally coupled with respect to an inboard extent.

7. A tooth crown preparation system as set forth in claim 6 wherein the outboard extent is universally pivotal with respect to the inboard extent.

8. A tooth crown preparation system comprising:

a handle having an inboard extent and an outboard extent;

a tooth cover mounted on the handle and defining an interior space and an open bottom; and a grinding assembly rotatably mounted to the handle and situated within the tooth cover for rotating upon its actuation to grind a tooth;

wherein the outboard extent is universally pivotal with respect to the inboard extent by way of a ball and socket joint.

9. A tooth crown preparation system as set forth in claim 8 and further including a plurality of differently sized tooth covers and grinding assemblies which are removably coupled to the handle.

10. A tooth crown preparation system as set forth in claim 8 wherein at least one button is mounted on the handle for selectively actuating the grinding assembly.

11. A tooth crown preparation system as set forth in claim 8 wherein the grinding assembly is slidable along its axis and further included is at least one button mounted on the handle for selectively sliding the grinding assembly along its axis.

12. A tooth crown preparation system as set forth in claim 8 and further including a suction assembly for removing particles from within the grinding assembly.

13. A tooth crown preparation system as set forth in claim 12 wherein the grinding assembly has a plurality of apertures formed therein for allowing the suctioning of particles therefrom.

14. A tooth crown preparation system as set forth in claim 13 wherein the suction assembly includes a conduit situated within an interior space of the handle with a first open end terminating within the tooth cover and a second open end extending from the outboard extent of the handle for being releasably connected to a suction mechanism such that particles within the grinding assembly are removed.

* * * * *